United States Patent [19]

Takayama

[11] Patent Number: 4,691,706

[45] Date of Patent: Sep. 8, 1987

[54] CALCULUS DISINTEGRATING APPARATUS

[75] Inventor: Syuichi Takayama, Tokyo, Japan

[73] Assignee: Olympus Optical Co., Tokyo, Japan

[21] Appl. No.: 899,787

[22] Filed: Aug. 22, 1986

Related U.S. Application Data

[60] Continuation of Ser. No. 723,050, Apr. 15, 1985, abandoned, which is a division of Ser. No. 449,699, Dec. 14, 1982, Pat. No. 4,535,771.

[30] Foreign Application Priority Data

| | | | |
|---|---|---|---|
| Dec. 22, 1981 | [JP] | Japan | 206107 |
| Dec. 26, 1981 | [JP] | Japan | 214252 |
| Jan. 19, 1982 | [JP] | Japan | 6576 |

[51] Int. Cl.[4] ........................ A61B 17/22; A61B 17/36

[52] U.S. Cl. ........................ 128/328

[58] Field of Search .............. 128/328, 303.13, 303.14, 128/303.17; 307/268, 264; 328/67

[56] References Cited

U.S. PATENT DOCUMENTS

| | | | |
|---|---|---|---|
| 3,413,976 | 12/1968 | Roze . | |
| 3,563,247 | 2/1971 | Bowers | 128/422 |
| 3,735,764 | 5/1973 | Balev et al. . | |
| 3,785,382 | 1/1974 | Schmidt-Kloiber et al. . | |
| 3,902,499 | 9/1975 | Shene . | |
| 4,019,510 | 4/1977 | Ellis | 604/20 |
| 4,114,623 | 9/1978 | Meinke et al. | 128/303.14 |
| 4,122,854 | 10/1978 | Blackett | 128/303.13 |
| 4,155,363 | 5/1979 | Letchworth et al. . | |
| 4,191,189 | 3/1980 | Barkan . | |
| 4,271,837 | 6/1981 | Schuler | 128/303.14 |
| 4,301,801 | 11/1981 | Schneiderman | 128/303.14 |
| 4,340,047 | 7/1982 | Tapper et al. | 604/20 |
| 4,404,476 | 9/1983 | Lezan | 307/268 |

FOREIGN PATENT DOCUMENTS

| | | | |
|---|---|---|---|
| 707011 | 3/1965 | Canada | 128/419 R |

*Primary Examiner*—Michael H. Thaler
*Attorney, Agent, or Firm*—Frishauf, Holtz, Goodman & Woodward

[57] ABSTRACT

A calculus disintegrating apparatus includes first and second electrodes which are arranged at the distal end of a probe inserted into a coeliac cavity, and discharge energy sources connected to the first and second electrodes to impress D.C. impulse voltage across them. The apparatus is arranged to disintegrate a calculus by impact waves resulting from spark discharges produced across the first and second electrodes. A polarity changing circuit is provided between the discharge energy sources and first and second electrodes to vary the polarity of the output D.C. impulse voltage from the discharge energy sources.

2 Claims, 20 Drawing Figures

CALCULUS DISINTEGRATING APPARATUS

This application is a continuation of application Ser. No. 723,050, filed Apr. 15, 1985, now abandoned, which is a division of Ser. No. 449,699 filed Dec. 14, 1982, now U.S. Pat. No. 4,535,771.

BACKGROUND OF THE INVENTION

This invention relates to a calculus disintegrating apparatus. A calculus disintegrating apparatus has been developed which producs spark discharges in a coeliac liquid surrounding a calculus to digintegrate the calculus by the resultant hydraulic impact wave. Such a calculus disintegrating apparatus generally comprises two electrodes set at the distal end of a probe inserted into a coeliac cavity and a power supply section which impresses D.C. impulse voltage on the electrodes to generate spark discharges across the electrodes. The power supply section provided with a capacitor causes the discharge current to flow across the electrodes for production of spark discharges. The electrodes are generally prepared from tungsten alloy, and are slowly consumed with time due to the impression of discharge energy. During the use of the electrodes, the end of the anode in particular is rounded, resulting in a rise in the voltage required for the initiation of spark discharges. When a spark discharge initiating voltage rises beyond the voltage with which the capacitor is charged, then spark discharges fail to be produced. This means that consumption of an electrode shortens the effective life thereof. Moreover, it is impossible to recognize the extent of the depletion of the electrode by the naked eye, thus failing to define an optimum point of time at which the used electrode is to be exchanged for a fresh one. While a patient is undergoing a treatment, it sometimes happens that the effective life of an electrode comes to an end. Such an event increases the time of treatment and the pain suffered by a patient.

SUMMARY OF THE INVENTION

It is accordingly an object of this invention to extend the effective life of a calculus disintegrating apparatus which disintegrates a calculus by a hydraulic impact wave resulting from spark discharges.

To attain the above-mentioned object, this invention provides a calculus disintegrating apparatus which comprises first and second electrodes provided separately from each other, a capacitor connected between the first and second electrodes, a power source for charging the capacitor, a circuit allowing for the passage of a discharge current across the first and second electrodes, and a switching circuit for changing the direction in which the discharge current flows.

DETAILED DESCRIPTION OF THE PREFERRED EMBODIMENTS

Figure 1:
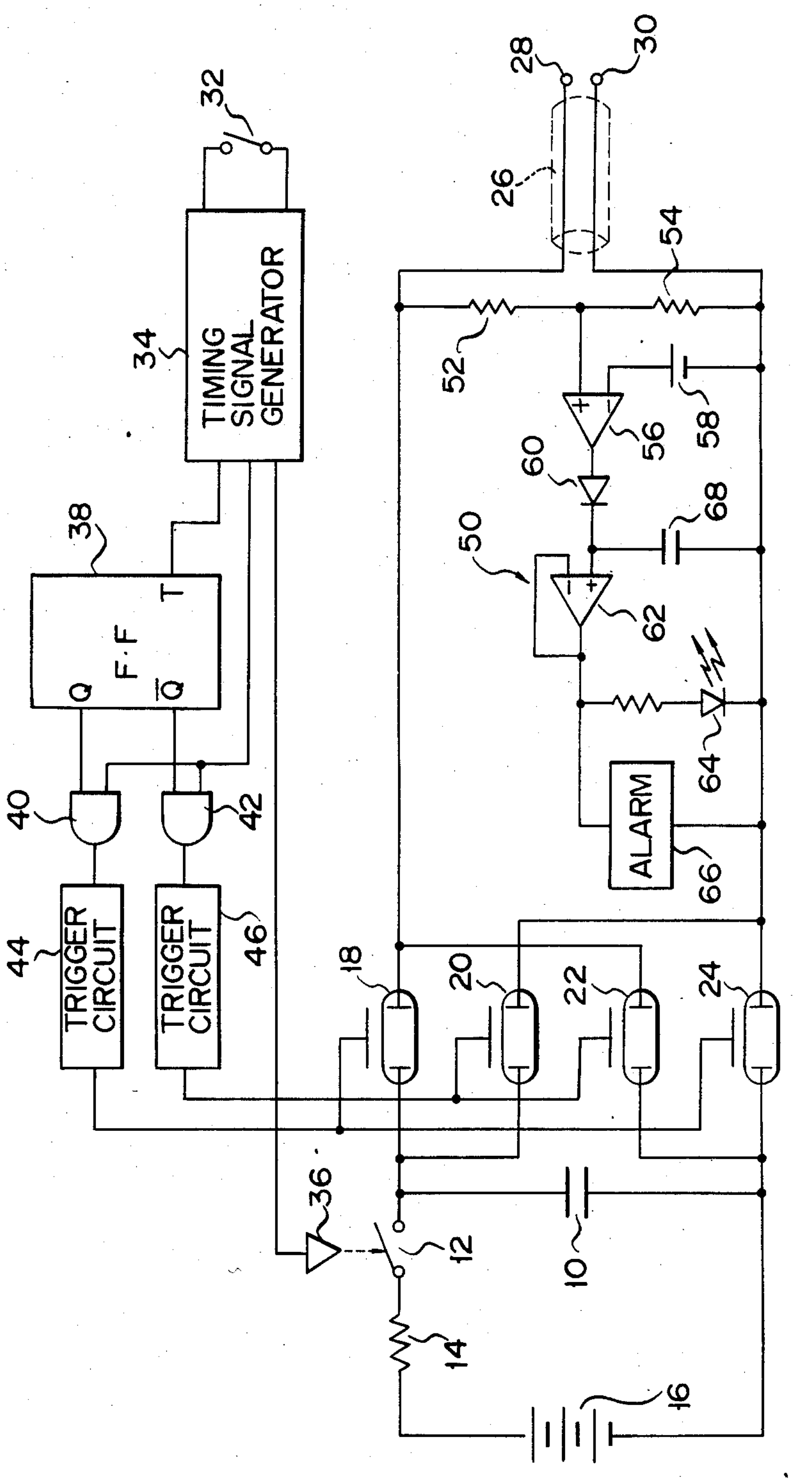
FIG. 1 is a block circuit diagram of a calculus disintegrating apparatus according to a first embodiment of this invention.

Description will now be given with reference to the accompanying drawings of a calculus disintegrating apparatus according to a first embodiment of this invention. FIG. 1 is a block diagram of the first embodiment. A capacitor 10 is connected to a D.C. power source 16 through a series-connected switch 12 and resistor 14. One end of the capacitor 10 is connected to an end of discharge tubes 18 and 20. The other end of the capacitor 10 is connected to an end of each of discharge tubes 22 and 24. The other ends of the discharge tubes 18 and 22 are connected together, and also to an electrode 28 through a probe 26. The other ends of the discharge tubes 20 and 24 are connected together, and also to an electrode 30 through the probe 26. The probe 26 is inserted into a coeliac cavity through, for example, a forceps channel of an endoscope. The electrodes 28 and 30 are so closely spaced from each other that spark discharges are easily produced across the electrodes 28 and 30 by the discharge current supplied from the capacitor 10. When the discharge tubes 18 and 24 are rendered conductive, current flows across the electrodes 28 and 30 in a direction different from when the discharge tubes 20 and 22 are rendered conductive. In other words, the discharge tubes 18, 20, 22 and 24 jointly constitute a polarity-changing circuit to alter the direction in which spark discharges are produced.

A first output terminal of a timing signal generator 34 having a trigger switch 32 is connected to an actuator 36. When supplied with a signal having a logic level "1", the actuator 36 closes the switch 12. A third output terminal of the timing signal generator 34 is connected to an input terminal of a T flip-flop circuit 38, and a second output terminal of the timing signal generator 34 is connected to first input terminals of AND gates 40 and 42. The output terminals Q and $\overline{Q}$ of the flip-flop circuit 38 are respectively connected to second input terminals of the AND gates 40 and 42. The output terminals of the AND gates 40 and 42 are respectively connected to trigger circuits 44 and 46. An output signal from the trigger circuit 44 is supplied to trigger electrodes of the discharge tubes 18 and 24. An output signal from the trigger circuit 46 is supplied to trigger electrodes of the discharge tubes 20 and 22.

A warning circuit 50 is connected between the electrodes 28 and 30 which detects the level of voltage impressed across the terminals of the electrodes 28 and 30, and, when the discharge initiating voltage rises beyond a prescribed level, lights an alarm lamp and also gives a sound alarm. The warning circuit 50 is arranged as desribed below. Resistors 52 and 54 are connected in series between the electrodes 28 and 30. The junction of the resistors 52 and 54 is connected to a noninverting input terminal of a comparator 56. A D.C. source 58 is connected to an inverting input terminal of the comparator 56. An output signal from the comparator 56 is supplied to a light-emitting diode (LED) 64 and alarm circuit 66 through a diode 60 and buffer 62. The input terminal of the buffer 62 is connected to a capacitor 68.

Figure 2A:
FIGS. 2A to 2E are timing charts showing the operation of the calculus disintegrating apparatus of FIG. 1.
Figure 2B:
Figure 2C:

Description will now be given with reference to the timing charts of FIGS. 2A to 2E, of the operation of a calculus disintegrating apparatus according to the first embodiment of this invention. When power is supplied to the timing signal generator 34, a pulse having a logic level "1" is issued from the first output terminal of the timing signal generator 34 to the actuator 36 (FIG. 2A). As a result, the switch 12 is closed to cause the capacitor 10 to be charged by the D.C. source 16 (FIG. 2B). The period of time during which the switch 12 remains closed, that is, the pulse width of the first output signal is defined by the capacitance of the capacitor 10 and the resistance of the resistor 14. The capacitor 10 is charged to the same potential as the D.C. source 16. Thus the subject calculus disintegrating apparatus is brought to a standby state.

Figure 2D:
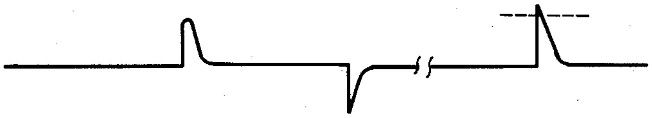
Figure 2E:
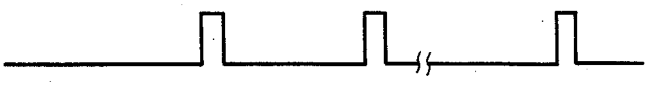

Now let it be assumed that the flip-flop circuit 38 is set. The electrodes 28 and 30 are drawn near the calculus of a patient, and the trigger switch 32 is closed. At this time, the timing signal generator 34 sends forth a pulse signal having a logic level "1" (FIG. 2C) from the second output terminal. The AND gate 40 and consequently the trigger circuit 44 are rendered conductive. The discharge tubes 18 and 24 are rendered conductive, causing an output discharge current from the capacitor 10 to flow through the discharge tube 24, electrodes 30 and 28 and discharge tube 18. As a result, a D.C. inpulse voltage is impressed across the electrodes 28 and 30 (FIG. 2D). A discharge current flows from the electrode 30 to the electrode 28. An impact wave is produced to disintegrate a calculus. The timing signal generator 34 sends forth a pulse signal having a logic level "1" (FIG. 2E) from a third output terminal in a prescribed length of time after the issue of a second output signal. As a result, the flip-flop circuit 38 is reset. The first output pulse is automatically sent forth at a prescribed length of time after the issue of the third output signal. When the trigger switch 32 is again closed, the AND gate 42 and consequently the trigger circuit 46 are rendered conductive. Since the discharge tubes 20 and 22 are rendered conductive, an output discharge current from the capacitor 10 flows through the discharge tube 22, electrodes 28 and 30, and the discharge tube 20. In other words, the discharge current flows in the opposite direction to the aforementioned case.

With the above-mentioned calculus disintegrating apparatus according to the first embodiment, a discharge current flows in the opposite direction for each discharge, preventing the same electrode from always being specified as the anode, and enabling the anode electrode to be consumed at half the rate which is observed in the conventional calculus disintegrating apparatus. Therefore, electrode life can be substantially doubled.

When discharge is carried out very frequently, then the electrodes 28 and 30 are noticeably consumed, leading to a rise in the discharge initiating voltage and presenting difficulties in producing spark discharges. When, with the first embodiment, the voltage across the electrodes 28 and 30 rises above the D.C. voltage 58 indicated by a broken line in FIG. 2D, then the LED 64 emits light and the alarm circuit 66 gives an alarm, thereby notifying the operator of the time at which the electrodes 28 and 30 are to be exchanged for fresh ones.

Figure 3:
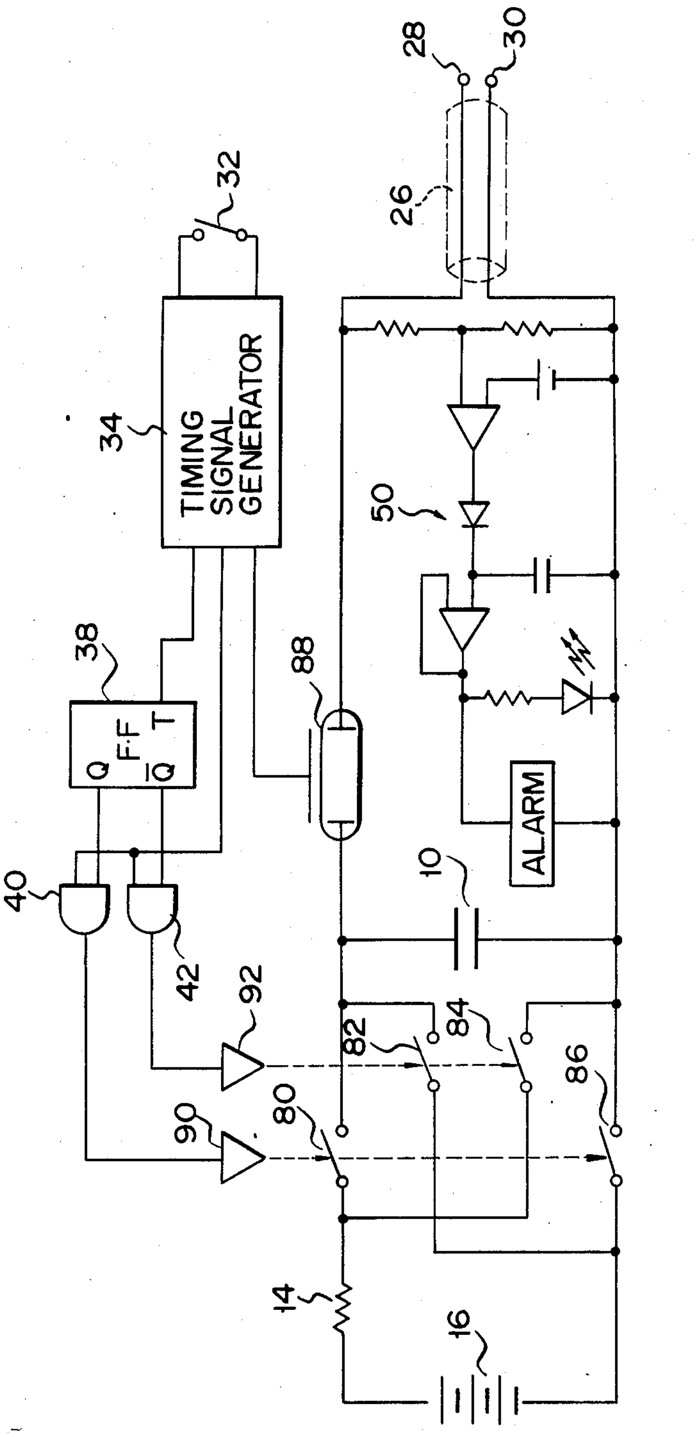
FIG. 3 is a block circuit diagram of a calculus disintegrating apparatus according to a second embodiment of the invention.

Description will now the given of other embodiments of a calculus disintegrating apparatus of this invention. The reference numerals used in the first embodiment will be used for corresponding elements in the other embodiments. A second embodiment shown in FIG. 3 is different from the first embodiment in that the second embodiment comprises a single discharge circuit, not two discharge circuits. One terminal of a capacitor 10 is connected selectively to positive and negative terminals of a D.C. source 16 through switches 80 and 82. The other end of the capacitor 10 is connected selectively to the positive and negative terminals of the D.C. source 16 through switches 84 and 86. A discharge tube 88 is connected to the discharge circuit of the capacitor 10. A first output terminal of a timing signal generator 34 is connected to first input terminals of AND gates 40 and 42. A second output terminal of the timing signal generator 34 is connected to a trigger terminal of the discharge tube 88. A third output terminal of the timing signal generator 34 is connected to an input terminal of a flip-flop circuit 38 as in the first embodiment. Output signals from the AND gates 40 and 42 are respectively supplied to actuators 90 and 92.

Figure 4A:
FIGS. 4A to 4E are timing charts showing the operation of the second embodiment.
Figure 4B:
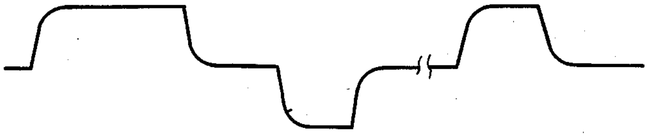
Figure 4C:
Figure 4D:
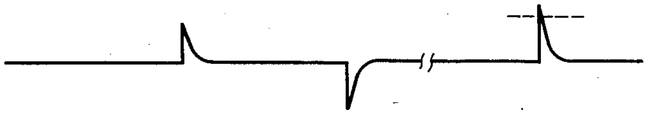
Figure 4E:

Description will now be given with reference to the timing charts of FIGS. 4A to 4E of the operation of the calculus disintegrating apparatus according to the second embodiment. FIGS. 4A to 4E respectively correspond to FIGS. 2A to 2E. A first output signal (FIG. 4A) from the timing signal generator 34 is supplied to the AND gates 40 and 42. Now let it be assumed that the flip-flop circuit 38 is set. Then, the AND gate 40 is rendered conductive, causing the switches 80 and 86 to be closed. The capacitor 10 is charged as shown in FIG. 4B. Later when the trigger switch 32 is closed, causing the timing signal generator 34 to issue a pulse signal (FIG. 4C) from the second output terminal, then the discharge tube 88 is rendered conductive, and an output discharge current from the capacitor 10 flows through the electrodes 30 and 28 and discharge tube 88. A pulse signal (FIG. 4E) is issued from the third output terminal of the timing signal generator 34, causing the flip-flop circuit 38 to be reset. Later when the timing signal generator 34 sends forth a first output signal (FIG. 4A), the AND gate 42 is rendered conductive, causing the switches 82 and 84 to be closed. The capacitor 10 is charged with the opposite polarity to the aforementioned case as indicated in FIG. 4B. When the discharge tube 88 is rendered conductive, a discharge current flows in the opposite direction to the above-mentioned case, causing voltage to be impressed across the electrodes 28 and 30 with the opposite polarity shown in FIG. 4D.

Even when the direction in which charge current is supplied to the capacitor 10 is changed as described above, the two electrodes 28 and 30 is alternately used as an anode as in the first embodiment. Therefore, the second embodiment has the same effect as the first embodiment. The warning circuit 50 has the same function as in the aforementioned case, description thereof being omitted.

With the above two embodiments, the direction in which the discharge current flows is altered each time by altering the discharge circuit or charge circuit. However, this alternative need not be performed each time. It is possible to alter the direction of the discharge current for every several discharges. Further, it is possible to alter the discharge direction after one electrode is so consumed as to fail to produce a spark discharge.

Figure 5:
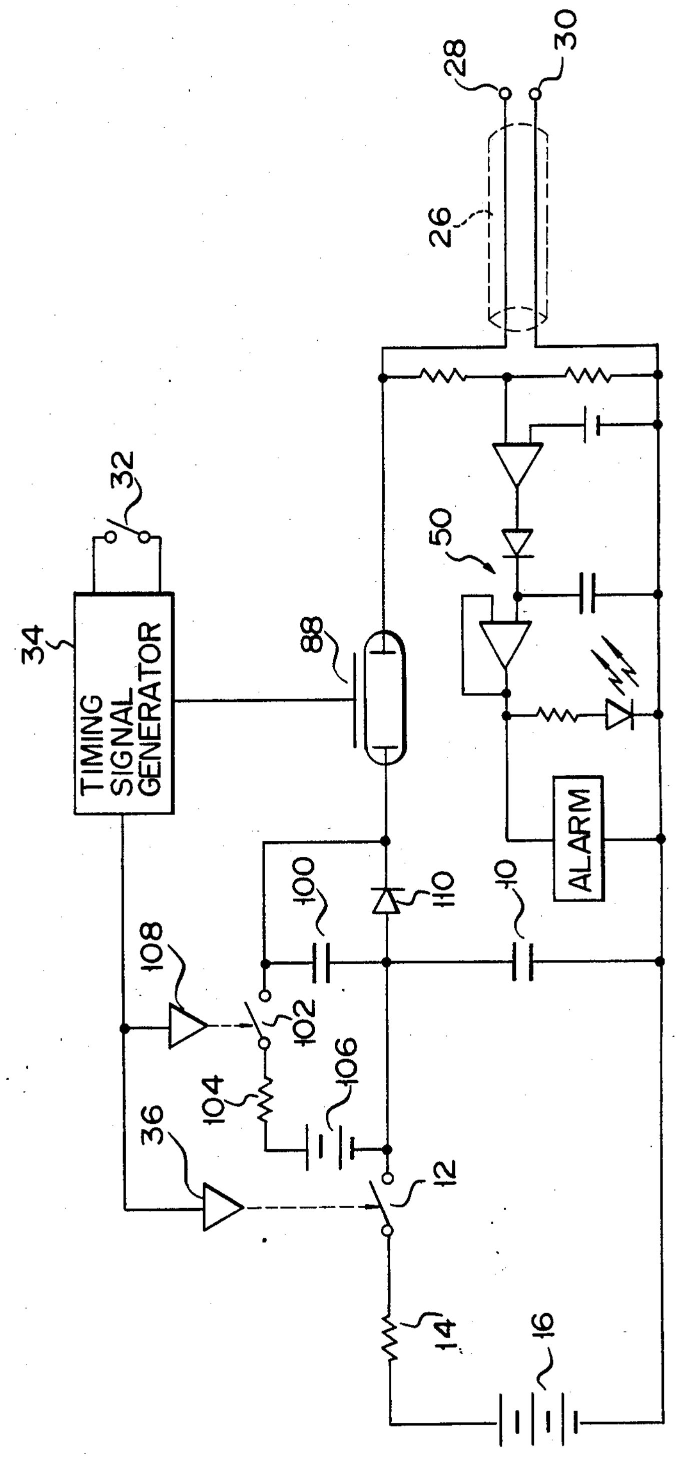
FIG. 5 is a block diagram of a calculus disintegrating apparatus according to a third embodiment of the invention.

FIG. 5 is a block diagram of a calculus disintegrating apparatus according to a third embodiment of this invention. The third embodiment comprises a single switch 12 for charging a capacitor 10 and a single discharge tube 88. An auxiliary capacitor 100 is connected in series to the capacitor 10. Discharge currents from both capacitors 100 and 10 are conducted to electrodes 28 and 30 through the discharge tube 88. The auxiliary capacitor 100 is connected to an auxiliary power source 106 through a switch 102 and a resistor 104. The auxiliary capacitor 100 has a smaller capacitance than the capacitor 10. A timing signal generator 34 has first and second output terminals. The first output terminal is connected to actuators 36 and 108, and the second output terminal is connected to a trigger terminal of the discharge tube 88. The actuators 36 and 108 are respectively operated to close switches 12 and 102. The junction of the capacitors 10 and 100 is connected to the discharge tube 88 through a diode 110. A warning circuit 50 is connected between the electrodes 28 and 30.

Figure 6A:
FIGS. 6A to 6D are timing charts indicating the operation of the third embodiment.
Figure 6B:
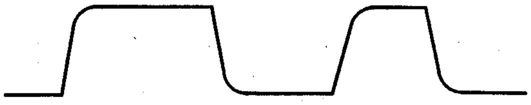
Figure 6C:
Figure 6D:

When, with the third embodiment of FIG. 5, the timing signal generator 34 issues a pulse signal (FIG. 6A) from the first output terminal, then the actuators 36 and 108 are operated to close the switches 12 and 102. Power from the D.C. sources 16 and 106 is supplied to the series-connected capacitors 10 and 100 (FIG. 6B). When the trigger switch 32 is closed, and the timing signal generator 34 issues a pulse signal (FIG. 6C) from the second output terminal, then the discharge tube 88 is rendered conductive, causing the capacitors 10 and 100 to be discharged. In this case, the auxiliary capacitor 100 has a smaller capacitance than the capacitor 10, and is instantly discharged. At the initiation of discharge, a sum of the voltages impressed on the capacitors 10 and 100 is supplied across the electrodes 28 and 30 (FIG. 6D). Soon, a voltage discharged from the capacitor 10 alone is applied across the electrodes 28 and 30, thereby facilitating the occurrence of spark discharges across the electrodes 28 and 30. Therefore, countermeasures can be taken for even the rise in the discharge initiating voltage which is caused by the depletion of an electrode. High voltage is only required at the initiation of discharge. Therefore, the reason why the auxiliary capacitor 100 is chosen to have a smaller capacitance than the capacitor 10 is that this process enables D.C. power 106 to be effectively supplied. When the discharge initiating voltage rises above a prescribed level as shown in FIG. 6D, the warning circuit 50 is actuated to inform the operator to exchange the electrode.

As described above, the third embodiment comprises not only the ordinary capacitor 10, but also the auxiliary capacitor 100. Since the voltage of the auxiliary capacitor 100 is impressed across the electrodes 28 and 30 in addition to the voltage of the capacitor 10, spark discharges can be easily produced, enabling an electrode life to be extended more than in the conventional calculus disintegrating apparatus.

Figure 7:
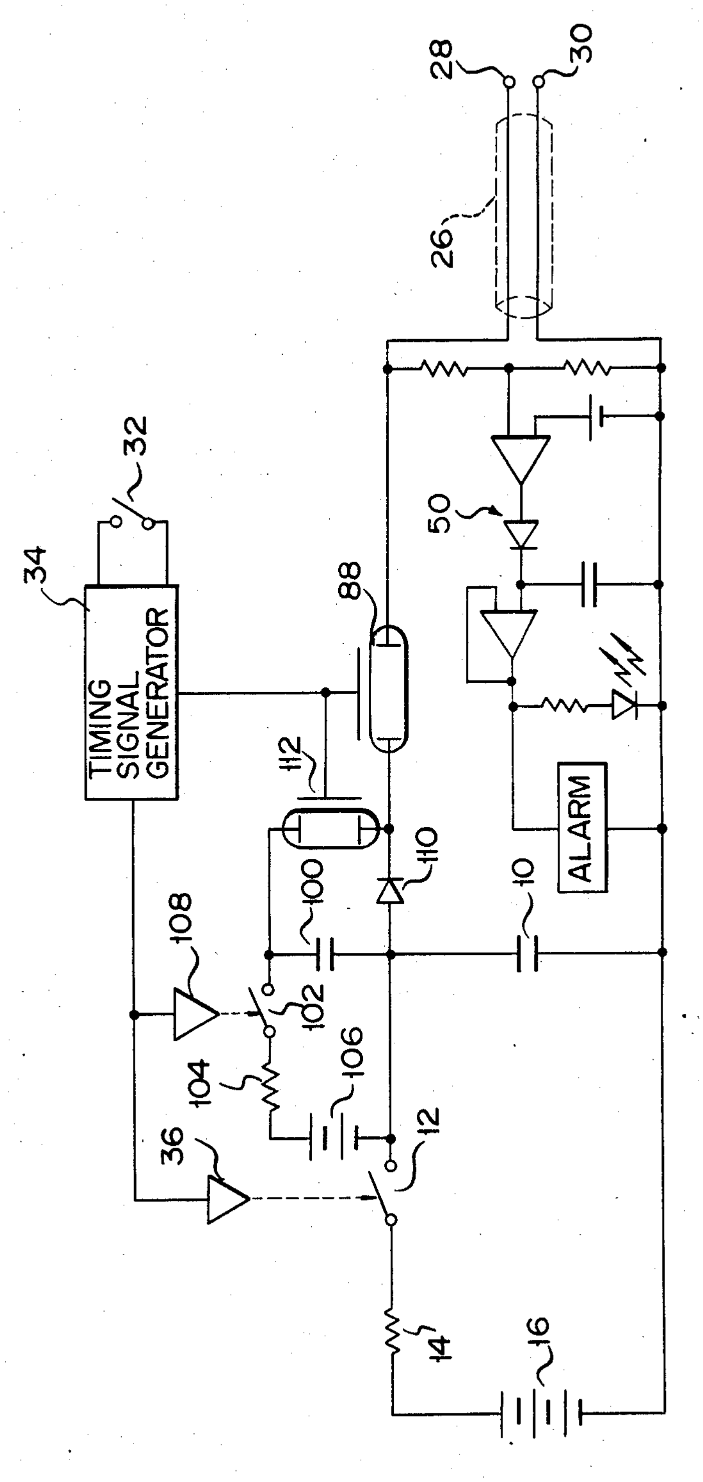
FIG. 7 is a block diagram of a modification of the third embodiment.

Description will now be given with reference to FIG. 7 of a modification of a calculus disintegrating apparatus of the third embodiment. With the third embodiment, a discharge tube 112 is provided in the discharge circuit of the capacitor 100, and the second output terminal of the timing signal generator 34 is connected to the trigger terminals of the discharge tubes 88 and 112. The discharge circuit for the capacitor 100 is formed only when the trigger switch 32 is closed, and the discharge tube 112 is rendered conductive. Therefore, the natural discharge of the capacitor 100 is suppressed.

Figure 8:
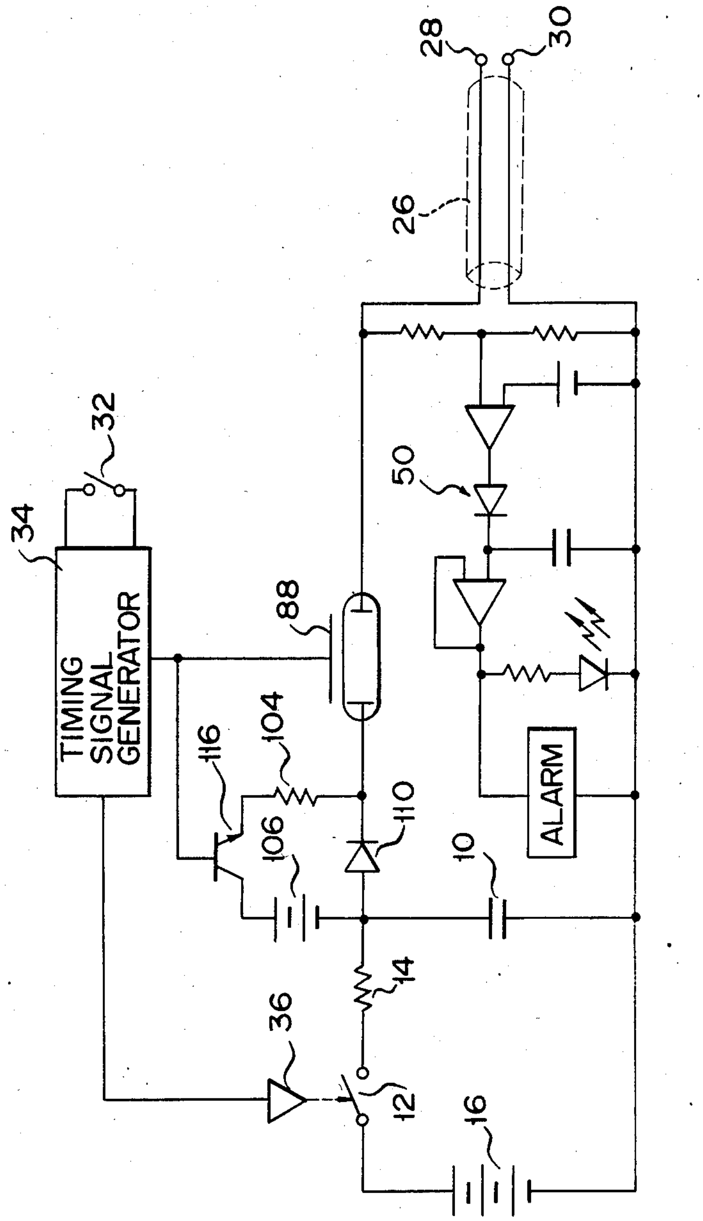
FIG. 8 is a block diagram of a calculus disintegrating apparatus according to a fourth embodiment of the invention.

Description is now given with reference to FIG. 8 of a fourth embodiment of this invention. The fourth embodiment is free from the capacitor 100 used in the third embodiment, and further the switch 102 of the third embodiment is replaced by a semiconductor switching element (NPN transistor) 116. The second output terminal of the timing signal generator 34 is connected to the base of the transistor 116 and the trigger terminal of the discharge tube 88. With the fourth embodiment, the timing signal generator 34 issues a second output pulse when the trigger switch 32 is closed, causing the transistor 116 and discharge tube 88 to be rendered conductive. The discharge tube 88 remains conductive until the discharge of the capacitor 10 is brought to an end, while the transistor 116 is rendered conductive only during the period of the second output pulse from the timing signal generator 34. At the initiation of discharge, therefore, a sum of the voltage of the capacitor 10 and that of the D.C. source 106 is impressed across the electrodes 28 and 30, thereby allowing for easy spark discharge.

With the third and fourth embodiments, higher voltage is impressed across the electrodes 28 and 30 at the initiation of discharge than in the conventional calculus disintegrating apparatus, thereby assuring the production of discharge even when the electrodes are appreciably depleted and substantially extending electrode life. High voltage is impressed only at the initiation of discharge, thereby saving excess power consumption.

Figure 9:
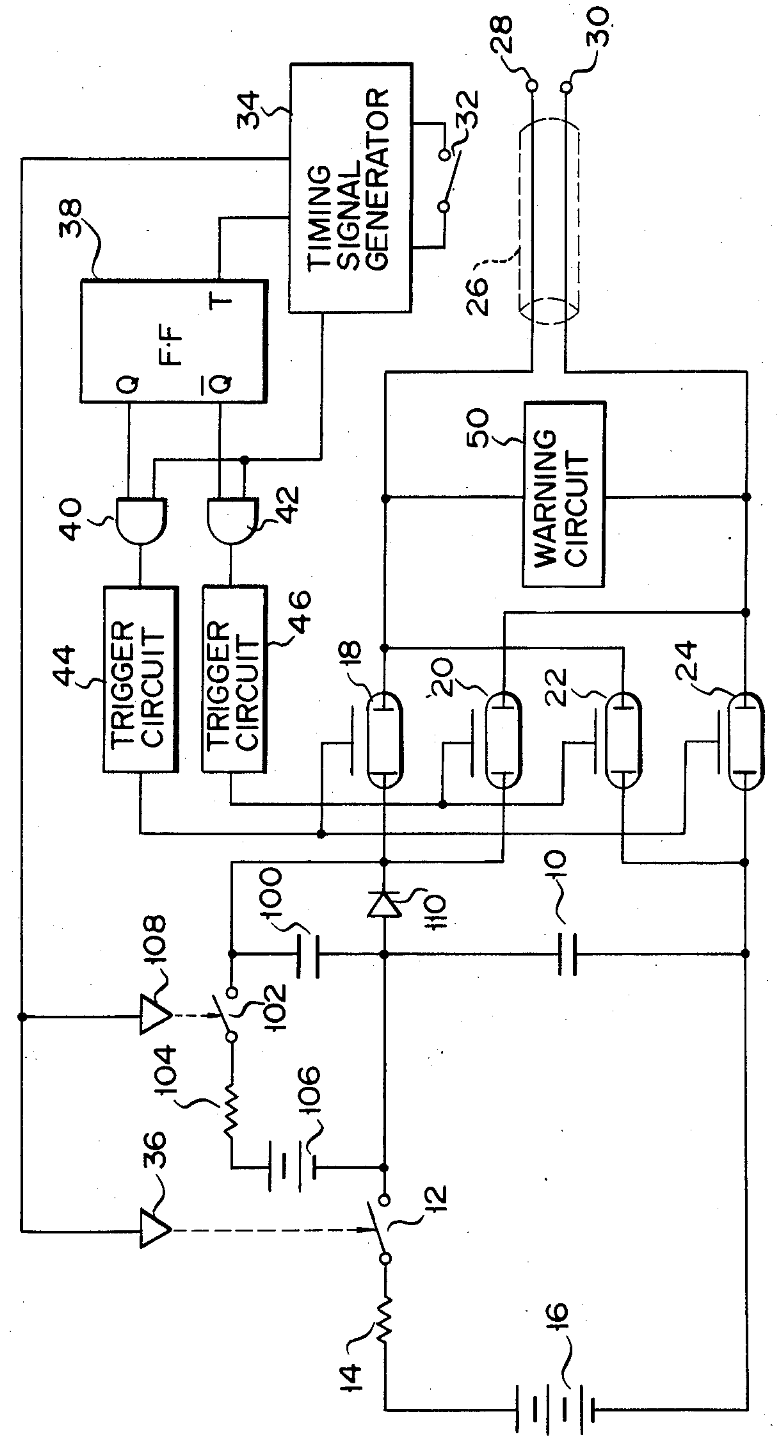
FIG. 9 is a block diagram of a fifth embodiment by assembling of the first and third embodiments.

This invention is not limited to the aforementioned embodiments, but is applicable with various modifications and changes. It is possible to assemble either of the first and second embodiments with either of the third and fourth embodiments. FIG. 9 shows a block diagram of a fifth embodiment of the invention by assembling the first embodiment of FIG. 1 with the third embodiment of FIG. 5. With the third and fourth embodiments, high voltage is always applied at the initiation of discahrge. However, it is possible to detect how much the electrodes are depleted when discharge is going to be started, and, if the depletion appreciably advances, to impress high voltage on the electrodes. The warning circuit 50 may detect a voltage impressed across the discharge tube 88 as a discharge initiating voltage. When the electrodes are depleted, the voltage of the capacitor 10 is raised when discharge is brought to an end. Therefore, it is possible to detect the voltage of the capacitor 10 at the termination of discharge and issue a warning signal according to the level of voltage detected.

What is claimed is:

1. A calculus disintegrating apparatus, which comprises:

first and second electrodes provided separately from each other;

first discharge energy means including a first D.C. power source and a first capacitor arranged to be charged by said first D.C. power source; said first discharge energy means being connected to said first and second electrodes to apply a D.C. impulse voltage across said first and second electrodes when said first capacitor is discharged;

switching means having two ends, one end thereof being connected to said first electrode, said switching means being operable so as to be conductive between said two ends thereof;

means for selectively rendering said switching means conductive;

second discharge energy means including a diode, a second D.C. power source, and a second capacitor arranged to be charged by said second D.C. power source; a cathode of said diode and a first terminal of said second capacitor being connected to another end of said switching means; and a second terminal of said second capacitor and an anode of said diode being connected to said first capacitor;

whereby said D.C. impulse voltage from said first capacitor and said D.C. impulse voltage from said second capacitor are superposedly applied across said first and second electrodes when said switching means is rendered conductive.

2. A calculus disintegrating apparatus according to claim 1, wherein said second discharge energy means comprises a series circuit including said second D.C. power source and a semiconductor switching element, said series circuit being connected in parallel to said second capacitor, and said semiconductor switching element being rendered conductive at the time of initiation of discharge.

* * * * *

UNITED STATES PATENT AND TRADEMARK OFFICE
CERTIFICATE OF CORRECTION

PATENT NO. : 4,691,706

DATED : September 8, 1987

INVENTOR(S) : Syuichi TAKAYAMA

It is certified that error appears in the above-identified patent and that said Letters Patent is hereby corrected as shown below:

In the title page, in the Assignee designation, change "Olympus Optical.," to --Olympus Optical Co., Ltd.--.

In the title page, under Foreign Application Priority Data,
change "206107" to --56-206107--;
change "214252" to --56-214252--;
change "6576" to --57-6576--.

Signed and Sealed this

Twenty-sixth Day of July, 1988

*Attest:*

DONALD J. QUIGG

*Attesting Officer* *Commissioner of Patents and Trademarks*